United States Patent
Park et al.

(10) Patent No.: US 10,737,990 B2
(45) Date of Patent: Aug. 11, 2020

(54) OLEFIN PRODUCTION METHOD USING CIRCULATING FLUIDIZED BED PROCESS

(71) Applicants: SK GAS CO., LTD., Seongnam-si, Gyeonggi-do (KR); KOREA RESEARCH INSTITUTE OF CHEMICAL TECHNOLOGY, Daejeon (KR)

(72) Inventors: Deuk Soo Park, Goyang-si (KR); Ung Gi Hong, Seoul (KR); Hyeongchan Ahn, Seoul (KR); Won Choon Choi, Daejeon (KR); Yong Ki Park, Seoul (KR)

(73) Assignees: SK GAS CO., LTD., Seongnam-si, Gyeonggi-Do (KR); KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/471,383

(22) PCT Filed: May 1, 2018

(86) PCT No.: PCT/KR2018/005047
§ 371 (c)(1),
(2) Date: Jun. 19, 2019

(87) PCT Pub. No.: WO2018/225952
PCT Pub. Date: Dec. 13, 2018

(65) Prior Publication Data
US 2019/0330125 A1 Oct. 31, 2019

(30) Foreign Application Priority Data
Jun. 7, 2017 (KR) .................. 10-2017-0070869

(51) Int. Cl.
*C07C 5/333* (2006.01)
*C07C 5/32* (2006.01)
(Continued)

(52) U.S. Cl.
CPC .......... *C07C 5/3332* (2013.01); *B01J 21/066* (2013.01); *B01J 23/26* (2013.01); *B01J 23/92* (2013.01);
(Continued)

(58) Field of Classification Search
CPC .......... C07C 5/333; C07C 5/3332; C07C 5/32
See application file for complete search history.

(56) References Cited

U.S. PATENT DOCUMENTS 8,563,793 B2 * 10/2013 Zimmermann ........... C07C 5/05
208/113
2009/0012339 A1 * 1/2009 Choi ....................... C07C 7/04
585/651

FOREIGN PATENT DOCUMENTS

KR   10-2003-0072241 A   9/2003
KR   10-0651418 B1   11/2006
(Continued)

OTHER PUBLICATIONS

International Search Report for PCT/KR2018/005047 dated Sep. 12, 2018 from Korean Intellectual Property Office.

*Primary Examiner* — Youngsul Jeong
(74) *Attorney, Agent, or Firm* — Paratus Law Group, PLLC

(57) ABSTRACT

Disclosed is an olefin production method which includes: (a) providing the regenerated catalyst and the hydrocarbon including not less than 90 wt % of LPG into Riser of Fast Fluidization Regime, and dehydrogenating in the presence of an alumina type catalyst; (b) separating an effluent from the dehydrogenation reaction into the catalyst and propylene (Continued)

mixture; (c) stripping to remove the hydrocarbon compound included in the catalyst separated at stage (b); (d) mixing the catalyst stripped at stage (c) with the gas including oxygen, and continuously regenerating it; (e) recycling the catalyst regenerated at stage (d) to stage (a), and providing it again into Riser; and (f) producing propylene product by cooling, compressing and separating propylene mixture of the reaction product separated at stage (b).

14 Claims, 6 Drawing Sheets

(51) Int. Cl.
      *B01J 21/06*       (2006.01)
      *B01J 23/26*       (2006.01)
      *B01J 23/92*       (2006.01)
      *B01J 38/30*       (2006.01)
(52) U.S. Cl.
      CPC ........... *B01J 38/30* (2013.01); *C07C 2521/04* (2013.01); *C07C 2521/06* (2013.01)

(56) References Cited

FOREIGN PATENT DOCUMENTS

| KR | 10-2016-0071114 A | 6/2016 | | |
|---|---|---|---|---|
| KR | 10-2017-0003371 A | 1/2017 | | |
| KR | 10-2017-0007636 A | 1/2017 | | |
| WO | WO-2014081545 A1 * | 5/2014 | .............. | B01J 19/32 |

* cited by examiner

OLEFIN PRODUCTION METHOD USING CIRCULATING FLUIDIZED BED PROCESS

CROSS REFERENCE TO PRIOR APPLICATIONS

This application is a National Stage Patent Application of PCT International Patent Application No. PCT/KR2018/005047 filed on May 1, 2018 under 35 U.S.C. § 371, which claims priority to Korean Patent Application No. 10-2017-0070869 filed on Jun. 7, 2017, which are all hereby incorporated by reference in their entirety.

BACKGROUND

The present invention relates to olefin production method using a circulating fluidized bed process.

The olefin like ethylene and propylene is widely used in the petrochemical industry. The olefin can be generally produced from naphtha thermal cracking process. However, because the competitiveness of the process using low-grade hydrocarbon as a raw material becomes higher according to shale gas revolution, on-purpose olefin production method using the catalytic dehydrogenation process is needed.

The catalytic dehydrogenation process for producing the olefin utilizes various low-grade hydrocarbon compound as a raw material, and the olefin yield is very good. However, although commercial fixed bed dehydrogenation process has high olefin yield at an initial stage of the reaction of the hydrocarbon contacting with the catalyst, the hydrocarbon conversion rate and the olefin yield decrease and the energy consumption for the regeneration process is increased because of catalyst deactivation and excessive coke generation as time goes. In order to solve the problem, the circulating fluidized bed process to have short contact time of the hydrocarbon and the catalyst is suggested.

However, at an initial stage of the circulating fluidized bed process to have short contact time of the hydrocarbon and the catalyst, the hydrocarbon reacts with the catalyst to generate the byproduct rapidly other than the olefin. Therefore, there is a demerit that the conversion rate of the hydrocarbon is high but the selectivity of the olefin is very low.

At the circulating fluidized bed process to produce the olefin from the hydrocarbon feedstock, in order to selectively produce the olefin such as ethylene and propylene with high conversion rate and high selectivity, setting the operation condition of Riser mainly conducting the dehydrogenation reaction can be considered as an important factor. Especially, fluid flow phenomena and reaction phenomena in Riser can be easily understood by the following theoretical study, which is explained hereinafter in detail.

As shown in FIG. 1, when gas is provided from the bottom to the reactor charged with the solid catalyst, if particles are fluidized and go over Minimum Fluidization Velocity, Flow Regime would be classified into five (5) regimes.

Specifically, the regimes are named as Minimum Fluidization Regime, Bubbling Fluidization Regime, Slugging Fluidization Regime, Turbulent Fluidization Regime and Lean phase Fluidization with Pneumatic Transport Regime, and the particle motion property in each regime is different from each other.

Therefore, in case of the process using the fluidized bed reactor, the suitable fluidized flow regime for each process property is formed and operated.

FIG. 2 shows the change of the catalyst volume fraction according to the height of Riser, that is, the change of flow regime. It is verified that the catalyst volume fraction in the reactor is changed according to the change of the fluidized flow regime. By the way, because the catalyst volume fraction importantly affects the process performance at the catalytic reaction such as the fluidized contact dehydrogenation reaction, consequently, process operation condition to determine the fluidized flow regime dominating the catalyst volume fraction in the reactor influences very importantly on the reaction result.

In order to determine the fluidized flow regime in Riser of the circulating fluidized bed process, the following factors must be considered. These factors are, for example, catalyst size, catalyst circulating rate, ratio of feed and catalyst, catalyst strength, etc.

In addition, the following factors directly affecting the dehydrogenation reaction must be considered. These factors are, for example, reaction temperature, the amount of absorption heat of the reaction, reaction time, catalyst deactivation caused by coke generation, etc.

At this, during studying the olefin production method using the circulating fluidized bed process with higher economic efficiency and productivity than traditional production process, by applying the catalyst having good selectivity and stability to the circulating fluidized bed process, more efficient olefin production method is developed and the present invention is completed.

SUMMARY

The present invention provides a fluidized bed olefin production method with higher economic efficiency and productivity than the traditional process.

The olefin production method of the present invention using the circulating fluidized bed process comprises:

(a) Providing the regenerated catalyst and the hydrocarbon including not less than 90 wt % of LPG into Riser of Fast Fluidization Regime, and dehydrogenating in the presence of an alumina type catalyst;

(b) Separating an effluent from dehydrogenation reaction into the catalyst and propylene mixture;

(c) Stripping to remove hydrocarbon compound included in the catalyst separated at stage (b).

(d) Mixing the catalyst stripped at stage (c) with gas including oxygen, and continuously regenerating;

(e) Recycling the catalyst regenerated at stage (d) to stage (a), and providing it again into Riser; and (f) Producing propylene product by cooling, compressing and separating propylene mixture of the reaction product separated at stage (b).

Fast Fluidization Regime is the steady state that gas flow rate is maintained over Turbulent Fluidization Regime and under Lean phase Fluidization with Pneumatic Transport Regime, and the fixed amount of the catalyst is continuously provided to Riser, wherein dense region of lower Riser and dilute region of upper Riser exist.

Furthermore, Fast Fluidization Regime is preferably that (a) gas flow rate is maintained over the gas flow rate required to make the catalyst continuously provided into lower Riser be entrained and smoothly exit to upper Riser, and (b) the difference of the catalyst volume fractions between both points is maintained at not less than 0.02 by controlling gas flow rate and catalyst feed rate.

More preferably, the difference of the catalyst volume fractions between ¼ point and ¾ point of the lower part in Riser is not less than 0.04.

The hydrocarbon mixture comprising not less than 90 wt % of propane as feedstock of the present invention contains not less than 90 wt %, more preferably 95 wt % of propane.

The catalyst used for the olefin production method of the present invention is an alumina type compound which can conduct the dehydrogenation reaction. Preferably, it is Zr—Al$_2$O$_3$ support impregnated with both metal component and alkali metal.

The mean size of the catalyst is 20~200 micron, preferably 60~120 micron.

In the olefin production method of the present invention, the lower part temperature of Riser is 500° C. to 750° C. and the upper part temperature of Riser is 450° C. to 700° C. It is preferable that the lower part temperature is maintained higher than the upper part temperature.

The pressure of Riser is preferably maintained at −1 to 5 kg/cm$^2$ g.

The residence time of the hydrocarbon mixture for the dehydrogenation reaction in Riser is 0.1 to 500 seconds, preferably 0.1~50 seconds, more preferably 0.5~5 seconds.

At Stage (e) of the olefin production method of the present invention, a weight ratio of the catalyst weight recycled to Riser bottom divided by the hydrocarbon mixture weight is 10~100, preferably 20~60.

The present invention is related to the circulating fluidized bed process to produce the olefin from the hydrocarbon feedstock by using the fast fluidized bed so that the olefin production is enhanced more efficiently.

That is, the circulating fluidized bed process according to the present invention improves the selectivity than the traditional commercial process so that the incremental interest per feedstock is increased. Because less air flow amount and small air compressor are required due to direct heat supplying system during the regeneration process, fuel consumption is reduced by 10~15% and the necessary compressor energy for the product separation and the catalyst regeneration is reduced 15~20% compared to the traditional commercial process so that the investment cost is decreased totally. Also, because of positive pressure operation, the equipment cost for the latter product separation process is reduced compared to the commercial process of vacuum operation.

DETAILED DESCRIPTION

As mentioned above, the process of the present invention comprises:

(a) Providing the regenerated catalyst and the hydrocarbon including not less than 90 wt % of LPG into Riser of Fast Fluidization Regime, and dehydrogenating it in the presence of the catalyst;

(b) Separating an effluent from the dehydrogenation reaction into the catalyst and propylene mixture;

(c) Stripping to remove the hydrocarbon compound included in the catalyst separated at stage (b).

(d) Mixing the catalyst stripped at stage (c) with gas including oxygen, and continuously regenerating it;

(e) Recycling the catalyst regenerated at stage (d) to stage (a), and providing it again into Riser; and (f) Producing propylene product by cooling, compressing and separating propylene mixture of the reaction product separated at stage (b).

Hereinafter, the present invention will be described in more detail by referring to attached figures. However, examples of the present invention can be modified to the other different type. It is to be understood, that the scope of the present invention is not limited to the examples to be explained in the following.

In order to explain the present examples, the same name and the same numeral are used for the same constitution, and thus overlapped additional explanation will be skipped in the following. Scale ratio will not be applied to the figures referred in the following.

In the following, the embodiment of catalytic cracking process according to the present invention will be explained in more detail. The scope of the present invention is not limited to the example.

Figure 1:
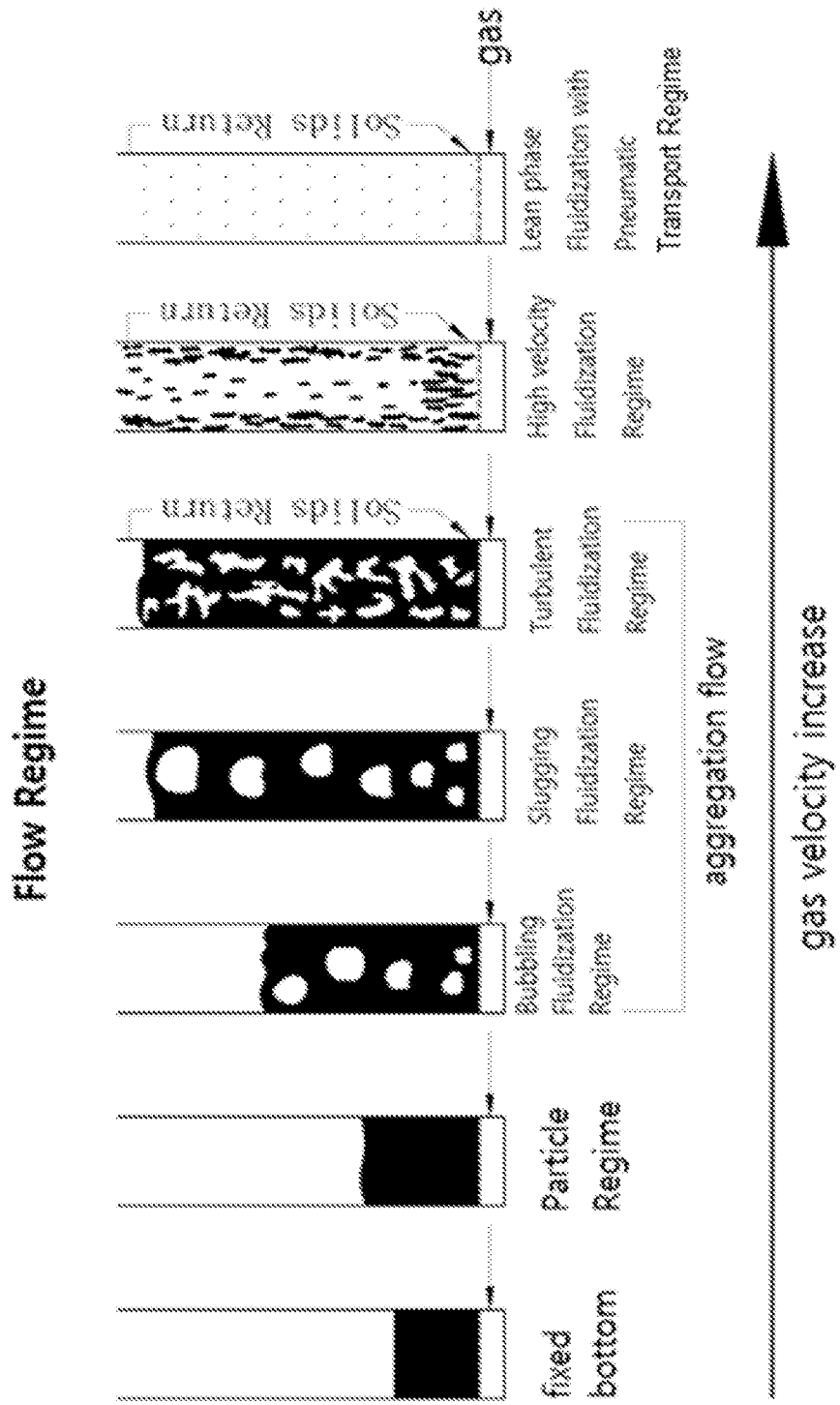
FIG. 1 is a schematic diagram describing the inner property change of the fluidized bed in the fluidized flow region according to general gas velocity change.
Figure 2:
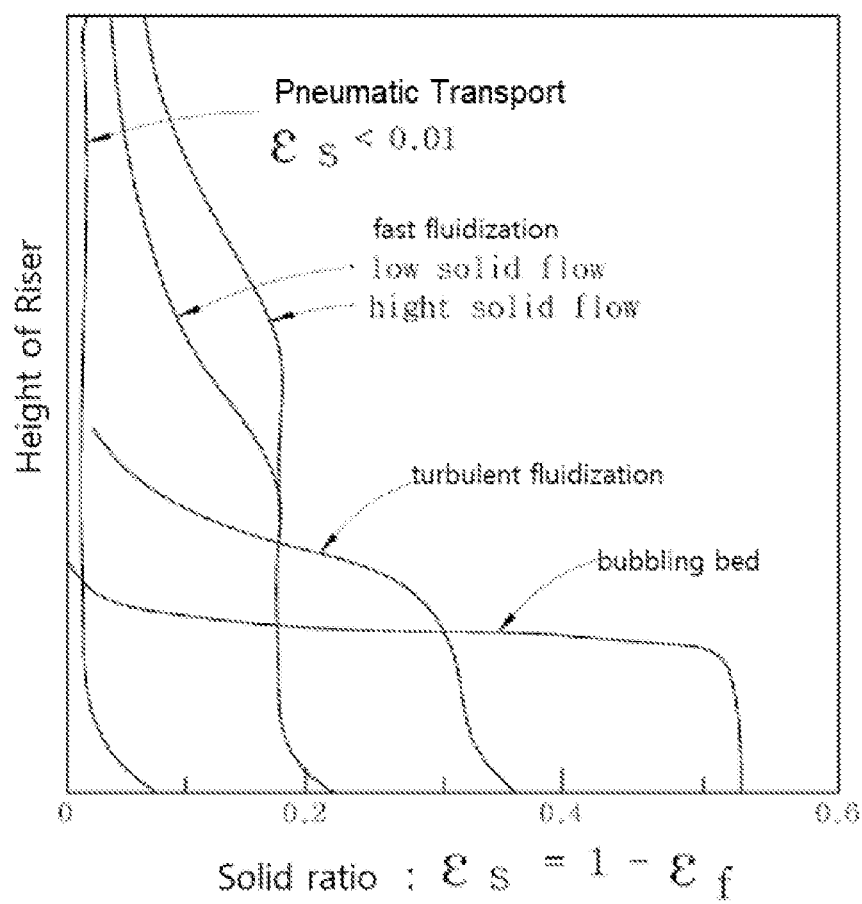
FIG. 2 is a schematic diagram describing the catalyst volume fraction in fluidized bed according to the height of Riser.
Figure 3:
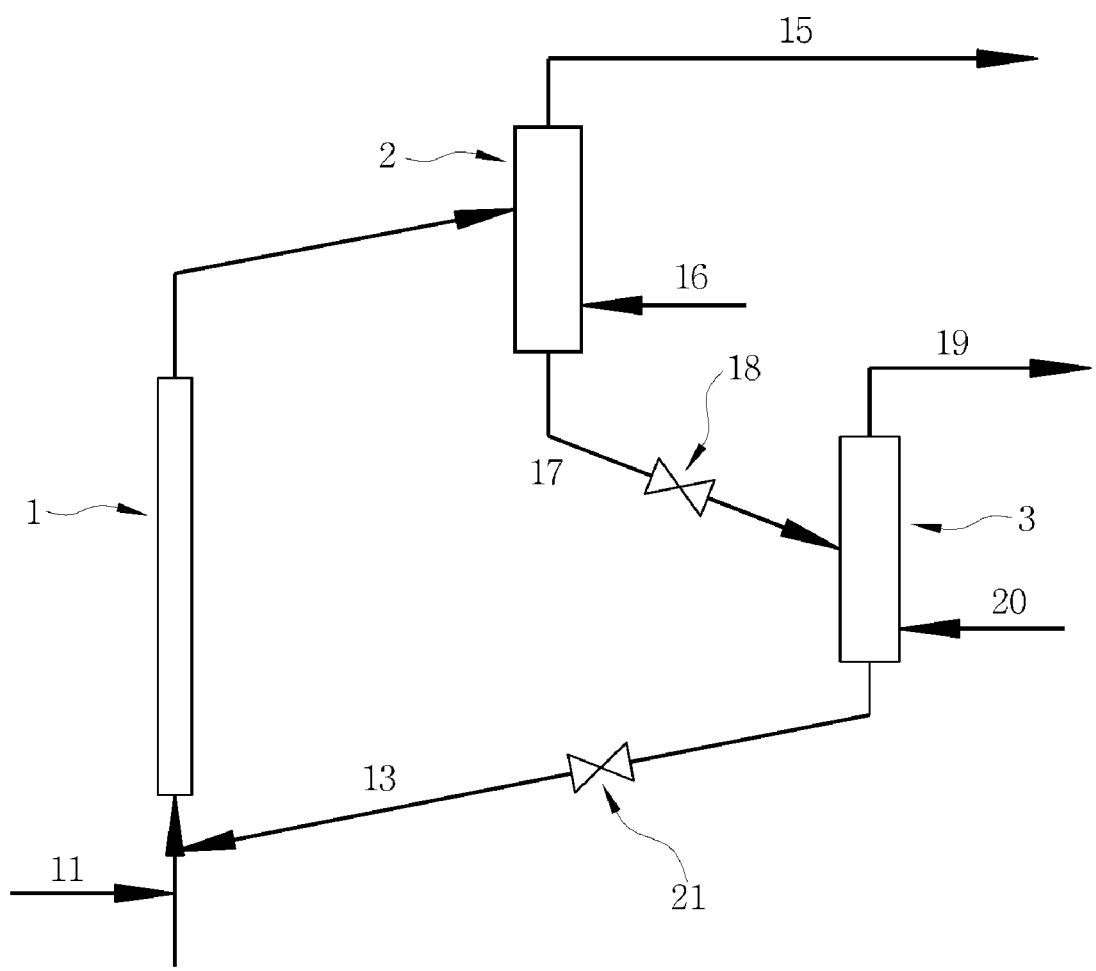
FIG. 3 is a schematic diagram of the circulating fluidized bed process used for the present invention.

The above explained feedstock is provided through the line (11) of FIG. 3. At this time, it can be provided with being heated to the temperature of 30~600° C. for more efficient reaction. Also, according to the component of the feedstock, it can be provided in a gaseous state or in a dispersed liquid state, which is not limited especially. The feedstock of the line (11) is introduced to Riser (1), and mixed in the lower part of Riser (1) with the regenerated catalyst provided through Regenerator Stand Pipe of the line (13). The other mixing process of feedstock and the regenerated catalyst can be made in a various method that is well known to the pertinent art. All these constitutions will be included into the scoped of the present invention.

Meanwhile, the catalyst used at the process is regenerated in regenerator (3), and the regenerated catalyst is provided through the line (13) to Riser (1). At this time, the lower part temperature of Riser is preferably maintained at 500~750° C. That is, by the heat provided by the regenerated catalyst (13), the temperature of feedstock (1) becomes to be increased to the temperature necessary for the dehydrogenation. When the lower part temperature of Riser is less than 500° C., the conversion rate of the catalyst is reduced. When the lower part temperature of Riser is more than 750° C., the catalyst selectivity is reduced because of the byproduct increase incurred by the thermal cracking of LPG feedstock.

Subsequently, the feedstock and the catalyst mixed in the lower part of Riser (1) are fluidized to the upper part with the simultaneous dehydrogenation. At this time, as the endothermic dehydrogenation proceeds, the temperature of mixture is decreased so that the upper part temperature of Riser (1) is also decreased. The product and the catalyst reached to the upper part of Riser (1) are introduced to Stripper (2), and thus the gaseous reaction product and the solid catalyst are separated in a short time. In order to enhance the efficiency of the separation process, a cyclone can be used selectively.

The separated gaseous product is discharged through the line (15). The separated catalyst is accumulated in Stripper (2) and moves downwards. At this time, Stripper Steam is provided through the line (16) to the lower part of Stripper (2). Stripper Steam (16) moves upwards through Stripper (2)

and removes the unseparated hydrocarbon product included in the catalyst, which is discharged to Product Gas of reaction of the line (15).

The catalyst reached to the lower part in Stripper (2) is moved through Stripper Stand Pipe of the line (17) to Regenerator (3) by controlling Slide Valve (18). At this time, the catalyst can comprise the coke generated during the reaction. The gas such as air and so on is introduced through the line (20) to Regenerator (3). At the high temperature of not less than 500° C., the coke included in the catalyst reacts with oxygen to be converted to carbon monoxide or carbon dioxide, and is discharged through the line (19) as flue gas. In result, the coke amount included in the catalyst can be reduced remarkably.

Meanwhile, the regenerated catalyst being in the lower part of Regenerator (3) is introduced through Regenerator Stand Pipe of the line (13) to Riser again by controlling Slide Valve (21), which can be recycled in the process.

In the process according to the present invention, the hydrocarbon compound, specifically the hydrocarbon mixture comprising not less than 90% of LPG can be used as feedstock. The hydrocarbon mixture comprising not less than 90% of LPG as feedstock of the present invention comprises preferably not less than 90 wt %, more preferably 95 wt % of propane. When propane concentration is low, the catalyst selectivity is reduced due to the side reaction of the other impurities so that the productivity is reduced.

In the present invention, the catalyst which can be used to dehydrogenate the feedstock can generally convert the hydrocarbon to the olefin through the dehydrogenation reaction, which is not limited especially if it is well known to the pertinent art. The catalyst including alumina is preferably used. The catalyst comprises an alumina support and further a metal component as a sub-support component, and comprises a transition metal and an alkali metal as an active component.

Preferably, the catalyst comprises anyone selected from zirconium, zinc and platinum as the sub-support component; and comprises anyone selected from the oxide of chromium, vanadium, manganese, iron, cobalt, molybdenum, copper, zinc, cerium and nickel as the transition metal. More preferably, zirconium is comprised as the sub-support component, chromium is comprised as the transition metal, and potassium is comprised as the alkali metal.

Furthermore, the mean size of the catalyst is preferably 20~200 micron, more preferably 60~120 micron. In order to achieve high efficient catalyst reaction, proper flow of Fast Fluidization Regime within Turbulent Fluidization Regime and Lean phase Fluidization with Pneumatic Transport Regime is required. However, when using the catalyst of smaller than 20 micron, the yield can be decreased due to high space velocity because Lean phase Fluidization with Pneumatic Transport Regime is predominant. Besides, when using the catalyst of larger than 200 micron, the production rate of the product is decreased because of very slow circulating fluidized flow. In order to maintain the same productivity, very huge catalytic reaction equipment is required so that the investment economic efficiency is declined.

As mentioned above, the dehydrogenation reaction to convert the hydrocarbon feed compound to the olefin occurs in Riser (1). Therefore, as an important reaction condition to affect the olefin yield, there are Riser temperature, the residence time of the reactant in Riser, the catalyst volume fraction and distribution in Riser, etc., which will be explained specifically in the following.

Above all, Riser temperature is highest at the lower part, and becomes to be decreased as it moves upwards. Therefore, it is effective in the present invention that the lower part temperature of Riser is maintained at 500~750° C., and the upper part temperature of Riser is maintained at 450~700° C. At this time, for more efficient flow, the temperature of lower Riser must be maintained higher than the temperature of upper Riser.

Meanwhile, the pressure of Riser is preferably maintained at −1 to 5 $kg/cm^2 \cdot g$. The pressure of Riser represents the reaction pressure. When it is less than −1 $kg/cm^2 \cdot g$, compression energy to separate the product from the produced materials is increased and the investment cost for the compression equipment is also increased so that total economic efficiency is reduced. Also, when it is more than 5 $kg/cm^2 \cdot g$, although the investment cost for the compression equipment and the compression energy is reduced at the latter part of the reactor, the product yield is decreased because of inducing high pressure reaction in Riser. Therefore, the appropriate pressure of Riser within the above range is needed.

Furthermore, in case of the dehydrogenation process to produce the olefin by using the above catalyst, the residence time of the reactant in Riser can be an important reaction condition to determine the olefin yield and the composition. Because how long the residence time is in Riser determines the number of the gas molecules and the flow rate as the dehydrogenation reaction proceeds in Riser, a criteria to determine the residence time is needed. Therefore, for the residence time of the reactant in Riser in the present invention, the value of Riser volume divided by volume velocity of the gas discharged from the upper part of Riser is used as the criteria.

In the dehydrogenation process of the present invention, the effective residence time of the hydrocarbon feed compound in Riser is 0.01~500 seconds, preferably 0.1~50 seconds, more preferably 0.5~5 seconds. When the residence time is less than 0.1 second, the sufficient contact time of the catalyst and the hydrocarbon feedstock is not secured so that the product yield is decreased. When being more than 500 seconds, the excessive investment cost for the reactor equipment is required to implement Fast Fluidization Regime needed in the present invention.

The fluidized dehydrogenation in the present invention is the endothermic reaction. The catalyst recycle of high temperature becomes to provide the heat needed for the reaction. Therefore, in the present invention, it is effective that the recycled catalyst amount more appropriate to this purpose conforms to the weight ratio of the weight of the recycled catalyst divided by the weight of feedstock (hydrocarbon mixture including LPG), which is 10~100, preferably 20~60.

When the weight ratio is less than 10, because the space velocity of the catalyst relative to the hydrocarbon feedstock becomes too high, the sufficient contact time for the reaction cannot be satisfied. When the weight ratio is more than 100, the excessive investment cost for the reactor equipment is required to implement Fast Fluidization Regime needed in the present invention. Furthermore, the excessive flow rate is induced in catalyst Regenerator so that the sufficient regeneration time is not satisfied. Therefore, the weight ratio within the above range of the proper catalyst weight divided by the weight of hydrocarbon mixture is required.

Meanwhile, as mentioned above, the catalyst volume fraction and the distribution in Riser are influenced by the flow fluidization regime greatly. At this time, Flow fluidization regime is determined by the gas velocity in Riser and the injection velocity of the catalyst introduced to Riser.

According to the circulating fluidized bed process of the present invention, in order to effectively produce the olefinic hydrocarbon compound from the hydrocarbon feed mixture, it is important to provide the sufficient volume fraction and the distribution of the catalyst which can conduct the dehydrogenation by maintaining the fluidization region of Riser to be Fast Fluidization Regime.

Therefore, more clear definition is necessary for the range of Fast Fluidization Regime. For this, an adjacent fluidization region, that is, Turbulent Fluidization Regime and Lean phase Fluidization with Pneumatic Transport Regime can be explained in comparison with each other. Above all, as the gas flow rate rises in Turbulent Fluidization Regime, the solid particles are entrained remarkably and exit from Riser so that it is transformed to Fast Fluidization Regime. Therefore, in order to maintain the constant amount of the catalyst at the gas velocity of Fast Fluidization Regime, the catalyst must be continuously injected to the lower part of Riser. The catalyst volume fraction is changed according to the height of Riser at Fast Fluidization Regime so that dense region of the lower part of Riser and dilute region of the upper part of Riser exist.

Moreover, when the velocity of the rising gas is increased more and more and the inflow of the solid particles is decreased at Fast Fluidization Regime, the catalyst volume in Riser becomes to be decreased so that it is transformed to Lean phase Fluidization with Pneumatic Transport Regime. In Lean phase Fluidization with Pneumatic Transport Regime, the catalyst volume fraction has very low value which is roughly constant according to the height of Riser.

At this, the catalyst volume is the volume occupied by the catalyst except for the empty space in the constant volume. In case of the porous catalyst, it is designated as the volume including macro pore and micro pore in the catalyst.

According to Kunii and Levenspiel(1991, Fluidization Engineering), it describes that in Fast Fluidization Regime, the catalyst exit from Riser is entrained quickly so that the catalyst must be continuously introduced in order to maintain the steady state of the operation condition. As shown FIG. 3, the feature of Fast Fluidization Regime is defined as follows.

The catalyst volume fraction is 0.2~0.4 of Riser volume in a short region from the lower inlet of Riser.

As the height is increased from the lower part of Riser, the catalyst volume has the constant fraction of about 0.2 to the specific height. Therefore, this is named as dense region.

The catalyst volume is gradually changed to have the fraction of 0.02~0.05 at the upper part over the dense region in Riser.

While the qualitative feature of Fast Fluidization Regime is maintained as the same according to the process change, the quantitative value of the catalyst volume becomes to be changed. The quantitative value of the catalyst volume becomes to be changed according to the physical properties of the catalyst such as intrinsic density and sphericity of the catalyst, and according to the physical properties such as gas density and viscosity depending on the change of a kind of gas.

Therefore, the preferable Fast Fluidization Regime which can be used for the circulating fluidized bed dehydrogenation process of the hydrocarbon compound according to the present invention is formed by maintaining the steady state that the gas flow rate in Riser is maintained over Turbulent Fluidization Regime and under Lean phase Fluidization with Pneumatic Transport Regime, and the fixed amount of the catalyst is continuously provided to Riser. At this, the catalyst volume fraction is changed according the height of Riser. It can be explained to mean the flow region wherein dense region of lower Riser and dilute region of upper Riser exist. More specifically, it can be formed and defined as follows.

1) The gas flow rate is maintained over the gas flow rate required to make the catalyst be entrained and smoothly exit from upper Riser, and the catalyst can be continuously provided to the lower part of Riser.

2) As the gas flow rate is increased under the above condition, the difference of the catalyst volume fractions between ¼ point and ¾ point of the lower part of Riser is decreased. The difference of the catalyst volume fractions between both points must be maintained at not less than 0.02, preferably not less than 0.04 by controlling the gas flow rate and the catalyst feed. The catalyst of the present invention presents the catalytic reactivity of high efficiency especially in Fast Fluidization Regime. When the difference of the volume fractions is less than 0.04, it approaches to Lean phase Fluidization with Pneumatic Transport Regime so that the yield decrease can be incurred by the high space velocity.

In the process according to the present invention to produce the olefinic hydrocarbon from the hydrocarbon mixture feedstock, preferably the hydrocarbon mixture including not less than 90 wt % of LPG by using the circulating fluidized bed process, when it is operated at Fast Fluidization Regime by controlling the gas flow rate in Riser and the catalyst feed introduced into Riser under the above condition, the maximum catalyst concentration can be provided in Riser. Therefore, the high conversion rate and the high selectivity of the olefinic hydrocarbon, more preferably propylene can be provided by this principle.

Comparative Example 1

Lean Phase Fluidization with Pneumatic Transport Regime

A. Preparation of Cold Model

A fluidized bed Cold Model is prepared in order to observe the fluidized flow region according to the change of the gas flow rate and the catalyst feed at room temperature. The solid particles passing through Roof Seal (54) controlling the solid circulation rate are introduced into Cold Model Riser (51) and are moved upwards through Riser by providing main gas through the line (60). The gas and the solid are separated in Cold Model Cyclone so that the gas is discharged as flue gas through the line (63) and the solid is moved downwards according to Cold Model Stand Pipe (53). In this case, the solid circulation can be smooth by the gas provided through the line (62). Cold Model Roof Seal (54) controls the amount of circulated catalyst by the gas controlling the catalyst circulation provided through Cold Model line (61).

In the above Comparative example 1, Cold Model Riser is manufactured to have the height of 2.5 m and the diameter of 0.9 cm. Stand Pipe and Roof Seal are manufactured to make the catalyst circulation be smooth.

B. Catalyst

The catalyst used for the examples is [(5% Cr+0.5% K)/5% Cr/Zr—$Al_2O_3$]. Volume mean diameter of the catalyst is 78 micron. Particle size distribution is composed of 10% of not more than 60 micron, 80% of 60~100 micron, and 10% of not less than 100 micron.

C. Experiment of Fluidized Flow Region

Figure 5:
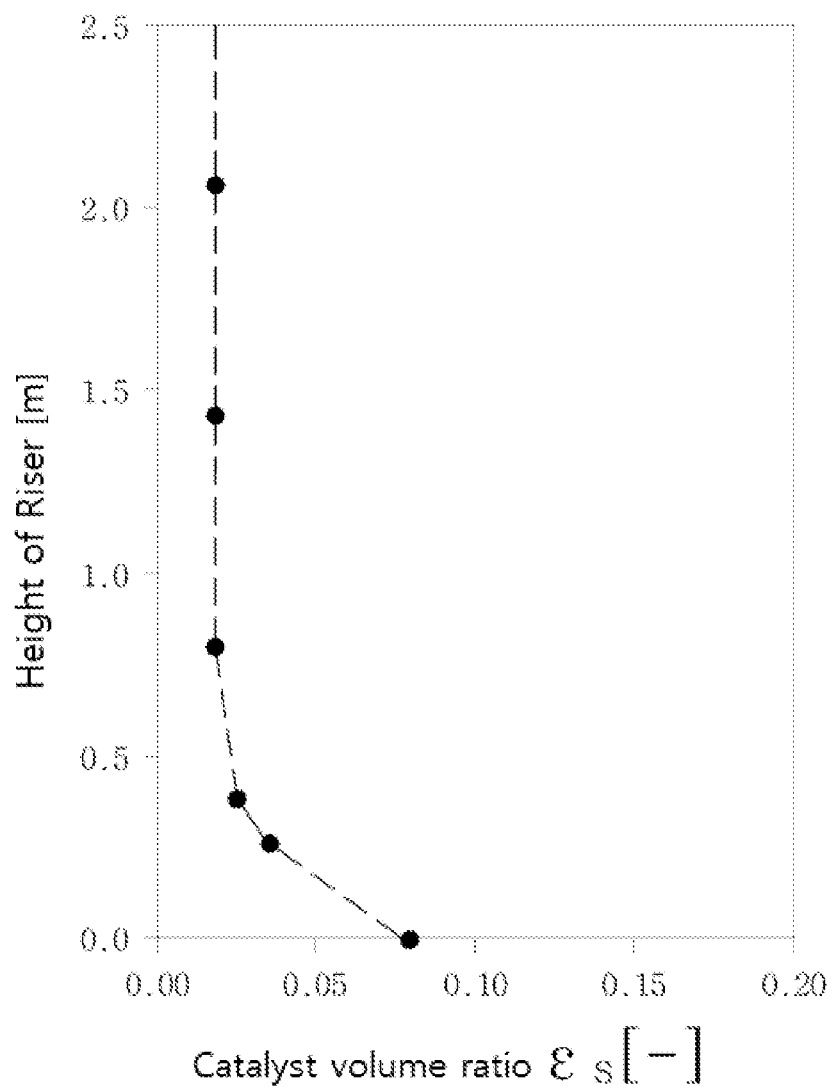
FIG. 5 is a graph describing the catalyst volume fraction in the fluidized bed at Lean phase Fluidization with Pneumatic Transport Regime as the experimental result of Cold Model according to Comparative example 1.

The experiment is conducted at room temperature and atmospheric pressure. The catalyst circulation rate is 20.2 kg/hr at the inlet of lower Riser, which corresponds to 88.1 kg/m$^2$·s in Riser. The pressure drop according to the height of Riser under the above condition is measured so that the catalyst volume fraction (Solid fraction) is obtained (FIG. 5). As shown in FIG. 5, the catalyst volume fractions of ¼ point and ¾ point of the lower part of Riser are 0.049 and 0.040 respectively, and the difference between both points is 0.009. Therefore, the flow type is verified to correspond to Lean phase Fluidization with Pneumatic Transport Regime according to the definition of the present invention.

Example 1

Fast Fluidization Regime

A. Preparation of Cold Model

Figure 4:
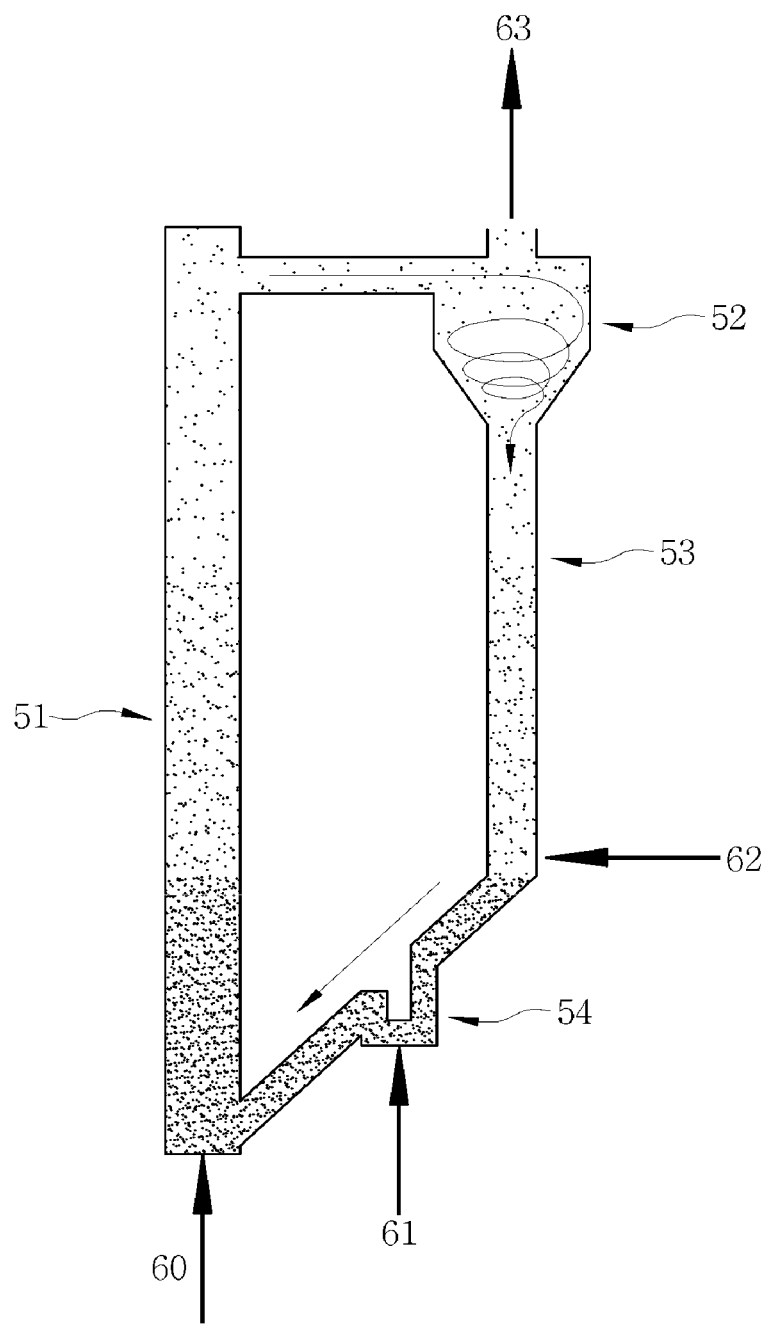
FIG. 4 is a schematic diagram of fluidized bed Cold Model for testing the fluidized flow region at room temperature.

In the same as Comparative 1, it is manufactured as shown in FIG. 4.

B. Catalyst

The same catalyst as Comparative example 1 is used.

C. Experiment of Fluidized Flow Region

Figure 6:
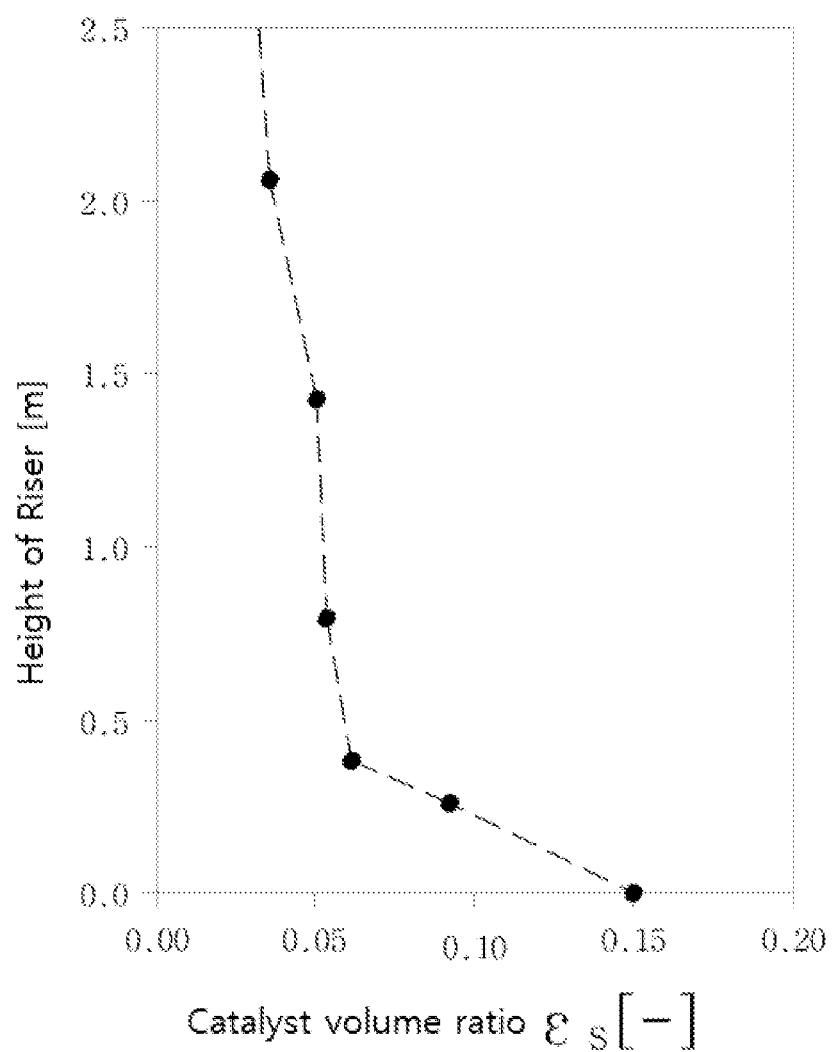
FIG. 6 is a graph describing the catalyst volume fraction in the fluidized bed at Fast Fluidization Regime as the experimental result of Cold Model according to Example 1.

The experiment is conducted in the same procedure as Comparative example 1. The catalyst circulation rate is 7.7 kg/hr at the inlet of lower Riser, which corresponds to 33.6 kg/m$^2$·s in Riser. The pressure drop according to the height of Riser under the above condition is measured so that the catalyst volume fraction (Solid fraction) is obtained (FIG. 6). As shown in FIG. 6, the catalyst volume fractions of ¼ point and ¾ point of the lower part of Riser are 0.092 and 0.049 respectively, and the difference between both points is 0.043. Therefore, the flow type is verified to correspond to Fast Fluidization Regime according to the definition of the present invention.

Comparative Example 2

A. Catalyst Preparation (1) Support (Zr—Al$_2$O$_3$) Preparation

Catapal B (alumina sold by Sasol) 13.89 kg added with water 25 kg is agitated for 30 minutes, and 1.83 kg of ZrO(NO$_3$)$_2$ and 25 kg of water is mixed and further agitated for 2.5 hours. Then, it is spray dried (feed velocity 0.56 g/min, atomizer 6000 rpm, inlet temperature 208° C., outlet temperature 125° C.), sieving separated (sieving: 75~200 µm), and calcined at 650° C. for 6 hours.

(2) Catalyst [(5% Cr+0.5% K)/5% Cr/Zr—Al$_2$O$_3$] preparation 0.482 g of CrO$_3$ and 2.5 g of water are mixed and impregnated with 5 g of the support as prepared above, dried at 120° C., and calcined at 700° C. for 3 hours (pre-catalyst).

0.482 g of CrO$_3$, 0.068 g of KNO$_3$ and 2.5 g of water are mixed and impregnated with 5.25 g of 5% Cr/Zr—Al$_2$O$_3$ as prepared above, dried at 120° C., and calcined at 700° C. for 3 hours so that the catalyst of the present invention is prepared.

B. Steam Treatment Process of the Catalyst

The catalyst is forced to be maintained in the atmosphere of 100% steam of 800° C. for 24 hours in order to estimate the catalyst performance of the equilibrium state.

C. Olefin Production Process

In Comparative example 2, in order to measure the activity of the catalyst during the olefin production as shown in FIG. 3, the circulating fluidized bed process is used. The circulating fluidized bed process is consisted of Riser, Regenerator, Stripper and Stabilizer. The height of Riser is 5 m, and its diameter is 0.94 cm. The height of Regenerator is 1.5 m, and its diameter 12 cm. The height of Stripper is 2 m, and its diameter is 10 cm. The height of Stabilizer is 1.7 m, and its diameter is 15 cm.

At Riser inlet, the feedstock of the hydrocarbon mixture comprising not less than 90% of LPG, dilution gas and the catalyst are introduced and mixed. The feedstock rate is 300 g/hr at 590° C. The space velocity of the catalyst is 4200 ml/g$_{cat}$·hr at 640° C. The injection rate of the catalyst is 88.1 kg/m$^2$·s by considering cross-sectional area of Riser (It is identical with Cold Model of Comparative example 1).

In case of Comparative example 2, the gas flow rate gasified at the inlet of Riser is the same as that of Comparative example 1. When considering the gas density and the viscosity, the fluidization properties in Riser of Comparative example 2 and 1 are determined to be the same with each other. Therefore, it is understood to be Lean phase Fluidization with Pneumatic Transport Regime.

Moreover, in case of Comparative example 2, the gas residence time in Riser is about 2 second based on the gas flow rate at the outlet of Riser. The ratio of the hourly injection weight of the regenerated catalyst to the hourly feedstock weight introduced to the inlet of Riser is 56.

The dehydrogenation reaction occurs in the fluidized bed during passing through Riser. The condition of the outlet of Riser is 599° C. and 2 barg. Then, the mixture passed through Riser is separated into the catalyst and the hydrocarbon compound at 500° C. in Stripper. The catalyst is recycled to Regenerator and the hydrocarbon compound is introduced to Stabilizer. The catalyst introduced to Regenerator is regenerated at 650° C. by contacting with air. The regenerated catalyst is recycled to Riser. Meanwhile, the hydrocarbon compound introduced to Stabilizer is separated into the gas component and the liquid component at −10° C.

The experimental result is described in the following Table 1.

TABLE 1

| | |
|---|---|
| WHSV (space velocity, ml/gcat · hr) | 4200 |
| Reaction temperature (° C.) | 640 |
| Conversion rate (%) | 76.9 |
| Selectivity (%) | 60.4 |
| Propylene yield (%) | 46.5 |
| CO yield (%) | 7.6 |
| CO2 yield (%) | 31.4 |

Example 2

A. Catalyst Preparation

The catalyst is prepared in the same procedure as Comparative example 2.

B. Steam Treatment Process of the Catalyst

The catalyst is treated by the steam in the same procedure as comparative example 2.

C. Olefin Production Process

In Example 2, the same circulating fluidized bed process as Comparative example 2 is used except for Riser. The height of Riser used herein is 2.4 m, and its diameter is 0.94 cm.

The same feedstock as Comparative example 2 is used. The feedstock rate is 300 g/hr at 590° C. The space velocity of the catalyst is 8400 ml/g$_{cat}$·hr at 640° C. Meanwhile, the injection rate of the catalyst is 33.6 kg/m$^2$·s by considering cross-sectional area of Riser (It is identical with Cold Model of Example 1).

In case of Example 2, the flow rate of total gas gasified at the inlet of Riser is the same as that of Example 1. When being determined by the gas density and the viscosity, the fluidization properties in Riser of Example 2 and 1 are determined to be the same with each other. Consequently, it is understood to be Fast Fluidization Regime.

Meanwhile, in case of Example 2, the gas residence time, the dilution ratio introduced to the inlet of Riser, and the weight ratio of the injection weight per hour of the regenerated catalyst to the feedstock weight per hour introduced to the inlet of Riser are all the same as those of Example 1.

The experimental result is described in the following Table 2.

TABLE 2

| | |
|---|---|
| WHSV (space velocity, ml/$g_{cat}$ · hr) | 8400 |
| Reaction temperature (° C.) | 640 |
| Conversion rate (%) | 61.7 |
| Selectivity (%) | 73.8 |
| Propylene yield (%) | 45.5 |
| CO yield (%) | 3.9 |
| CO2 yield (%) | 12.5 |

When comparing the yield of the reaction product, the olefin selectivity, especially propylene selectivity in Example 2 is identified to be remarkably higher than that of Comparative example 2. The result represents that the reaction selectivity can be controlled according to the residence time in Fast Fluidization Regime characterized in the present invention. Moreover, the selectivity is enhanced remarkably according to the present invention so that the incremental interest of the feedstock is increased and thus the economic efficiency is enhanced noticeably.

That is, the gas flow rate and the catalyst feed rate in Cold Model of Comparative example 1 and Example 1 are controlled to be the same as those of the fluidized flow regime of the catalyst under the reaction condition of Comparative example 2 and Example 2. The observation of the fluidized flow of the fluidized bed reactor by using this Cold Model is the general method. It can be understood that the regime in Riser of Comparative example 2 is the same Lean phase Fluidization with Pneumatic Transport Regime as Comparative example 1 and the regime in Riser of Example 2 is the same Fast Fluidization Regime as Example 1.

In the above, although the examples of the present invention is explained in detail, the claimed scope of the present invention is not limited to the examples. It is well known to a person of ordinary skill in the pertinent art that various modifications and changes can be made within the range of not deviating from the technical thought written in the claims of the present invention.

The present invention relates to olefin production method using a circulating fluidized bed process.

The invention claimed is:

1. An olefin production method comprising:
(a) providing a regenerated catalyst and a hydrocarbon mixture including not less than 90 wt % of LPG into a bottom of a Riser of Fast Fluidization Regime, and conducting a dehydrogenation reaction of the hydrocarbon mixture in the presence of the regenerated catalyst;
(b) separating an effluent from the dehydrogenation reaction into a catalyst stream and a propylene mixture stream at a top of the Riser of Fast Fluidization Regime;
(c) stripping to remove unseparated hydrocarbon compound included in the catalyst stream separated at stage (b) by contacting the catalyst stream counter-currently with a stripping steam;
(d) mixing catalyst stripped at stage (c) with a gas comprising oxygen, and continuously regenerating the catalyst;
(e) recycling the catalyst regenerated at stage (d) to stage (a), and providing it again into the Riser of Fast Fluidization Regime; and
(f) producing propylene product by cooling, compressing and separating the propylene mixture stream separated at stage (b);
wherein the catalyst used in the method comprises an alumina support,
wherein the Fast Fluidization Regime is a steady state that a gas flow rate is maintained over a Turbulent Fluidization Regime and under a Lean phase Fluidization with Pneumatic Transport Regime, and a fixed amount of the regenerated catalyst is continuously provided to the Riser, and
wherein a dense region at a lower part of the Riser and a dilute region at an upper part of the Riser exist.

2. The method of claim 1, wherein the Fast Fluidization Regime is that (a) the gas flow rate is maintained over the gas flow rate required to make the regenerated catalyst continuously provided into the bottom of the Riser be entrained and smoothly exit to the top of the Riser, and (b) a difference between catalyst volume fractions between the bottom and the top of the Riser is maintained at not less than 0.02.

3. The method of claim 2, wherein the difference between the catalyst volume fractions between ¼ point and ¾ point of the lower part in Riser is maintained at not less than 0.04.

4. The method of claim 1, wherein the hydrocarbon mixture comprises not less than 90 wt % of propane.

5. The method of claim 1, wherein the catalyst is a $Zr$—$Al_2O_3$ support impregnated with both a metal component and an alkali metal.

6. The method of claim 5, wherein a mean size of the catalyst is 20~200 microns.

7. The method of claim 6, wherein the mean size of the catalyst is 60~120 microns.

8. The method of claim 1, wherein a temperature of the bottom of the Riser is 500° C. to 750° C. and a temperature of the top of the Riser is 450° C. to 700° C., wherein the temperature of the bottom of the Riser is maintained higher than the temperature of the top of the Riser.

9. The method of claim 1, wherein a pressure of the Riser is −1 to 5 kg/cm$^2$·g.

10. The method of claim 1, wherein a residence time of the hydrocarbon mixture in the dehydrogenation reaction in the Riser is 0.1 to 500 seconds.

11. The method of claim 10, wherein the residence time is 0.1 to 50 seconds.

12. The method of claim 11, wherein the residence time is 0.5 to 5 seconds.

13. The method of claim 1, wherein at stage (e), a weight ratio of the regenerated catalyst weight recycled to the bottom of the Riser divided by the hydrocarbon mixture weight is 10-100.

14. The method of claim 13, wherein the weight ratio is 20-60.

* * * * *